United States Patent [19]
Vrabel et al.

[11] Patent Number: 6,004,904
[45] Date of Patent: Dec. 21, 1999

[54] USE OF 4-BENZOYLISOXAZOLES FOR THE PROTECTION OF TURFGRASS

[75] Inventors: Thomas Edward Vrabel, Raleigh, N.C.; Wilbur Fell Evans, Maple Glen, Pa.

[73] Assignee: Rhone-Poulenc Inc., Research Triangle Park, N.C.

[21] Appl. No.: 08/981,288

[22] PCT Filed: Jun. 12, 1996

[86] PCT No.: PCT/EP96/02543

§ 371 Date: Apr. 10, 1998

§ 102(e) Date: Apr. 10, 1998

[87] PCT Pub. No.: WO97/00014

PCT Pub. Date: Jan. 3, 1997

Related U.S. Application Data

[60] Provisional application No. 60/000,320, Jun. 19, 1995, abandoned.

[51] Int. Cl.$^6$ ..................................................... A01N 43/80
[52] U.S. Cl. ............................................................ 504/271
[58] Field of Search ............................................. 504/271

[56] References Cited

U.S. PATENT DOCUMENTS

| | | | |
|---|---|---|---|
| 5,374,605 | 12/1994 | Hallenbach et al. | 504/252 |
| 5,656,573 | 8/1997 | Roberts et al. | 504/271 |

FOREIGN PATENT DOCUMENTS

| | | |
|---|---|---|
| 0418175 | 3/1991 | European Pat. Off. . |
| 0487357 | 5/1992 | European Pat. Off. . |
| 0527036 | 2/1993 | European Pat. Off. . |
| 0527037 | 2/1993 | European Pat. Off. . |
| 0551821 | 7/1993 | European Pat. Off. . |
| 0560482 | 9/1993 | European Pat. Off. . |
| 0560483 | 9/1993 | European Pat. Off. . |
| 94/18179 | 8/1994 | WIPO . |

OTHER PUBLICATIONS

Database WPI, Section Ch, Week 8922, Derwent Publication Ltd., London, GB, AN89–150977, 1989 (abstract of JP 01 102005 of Apr. 19, 1989).

*Primary Examiner*—S. Mark Clardy
*Attorney, Agent, or Firm*—Burns, Doane, Swecker & Mathis, L.L.P.

[57] ABSTRACT

The invention relates to a method for the protection of a turfgrass at a locus which comprises applying to said locus an isoxazole derivative of formula (I), wherein R is hydrogen or —$CO_2R^3$, wherein $R^3$ is as defined below; $R^1$ is cyclopropyl; $R^2$ is selected from halogen, —$S(O)_pR^4$ and $C_{1-4}$ alkyl or haloalkyl; n is two or three; p is zero, one or two; $R^3$ is $C_{1-4}$ alkyl and $R^4$ is $C_{1-4}$ alkyl; and to compositions containing the same.

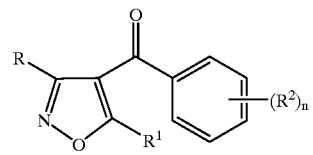

(I)

49 Claims, No Drawings

USE OF 4-BENZOYLISOXAZOLES FOR THE PROTECTION OF TURFGRASS

This application is the U.S. national stage of International Application No. PCT/EP96/02543, filed Jun. 12, 1996 and designating the United States, which claims the priority of U.S. Provisional Patent Application No. 60/000,320, filed Jun. 19, 1995, now abandoned.

BACKGROUND OF THE INVENTION

1. Field of the Invention

This invention relates to a new method of controlling weeds, and in particular it relates to a new method of protecting turfgrasses against both weed infestation and the presence of other undesired turfgrasses.

2. Discussion of the Prior Art

Protection of turf has always been a difficult problem because the users of turfs generally have very high standards and require a top quality in the turf. The severe requirements are probably due to their aesthetic needs which are far away of the classical requirements of agricultural users such as farmers, whose needs are directed to production considerations which do not involve anything on the appearance of the fields.

A problem of turf care is that the pesticidal treatment should be safe and not pvytotoxic for the desired turfgrass while being effective in controlling the weed species found infesting the turf.

Another problem of turf care is that it is often necessary maintain a monoculture turfgrass stand where no turfgrasses other than the desired single turfgrass species is present. This presents problems in that once another turfgrass species is present in the monoculture, many known agrochemicals will not selectively control the unwanted turfgrass species without also damaging the desired species.

Treatment of crops against weed infestation by isoxazoles is known, for example from European Patent Publication Nos. 0487357, 0527036, and 0560482. However, there is no indication in these publications that isoxazoles specifically control turfgrasses, much less that they meet the above cited requirements with regard to the protection of turfs. Furthermore, there is no suggestion in these publications that the isoxazoles possess any selectivity in their control of different turfgrasses.

An object of the invention is therefore to provide a method of control of weed species found in turf.

Yet another object of the invention is to provide a method of controlling undesired turfgrass species contaminating areas occupied, or to be occupied by, one or more desired turfgrass species.

A still further object of the invention is to overcome the existing problem of turf care, especially the problems as here above explained.

Suprisingly, it has been found that these objects may be fulfilled in whole or in part by the present invention.

SUMMARY OF THE INVENTION

The invention provides a method for the protection of a turfgrass at a locus which comprises applying to said locus an isoxazole derivative of formula I:

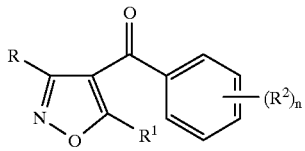

wherein
R is hydrogen or —$CO_2R^3$, wherein $R^3$ is as defined below;
$R^1$ is cyclopropyl;
$R^2$ is selected from halogen, —$S(O)_pR^4$, $C_{1-4}$ alkyl or $C_{1-4}$ haloalkyl;
n is two or three; p is zero, one or two;
$R^3$ is $C_{1-4}$ alkyl and
$R^4$ is $C_{1-4}$ alkyl.

DETAILED DESCRIPTION OF THE INVENTION

The isoxasole derivatives have been found to be effective in controlling a number of the major problem weeds found in turf stands, including *Digitaria sanguinalis* (crabgrass) and *Trifolium repens* (white clover). In addition to this, the isoxazole derivatives control certain (unwanted) turfgrass species while being safe to use with other turfgrasses, which offers the possibility of selectively controlling unwanted turfgrasses in the presence of other unwanted turfgrass species, which is an important feature where the user requires a homogeneous turfgrass area (e.g a lawn).

In the method of the invention the locus is preferably an area comprising a desired turfgrass, in particular one or more of *Festuca arundinacea* (tall fescue), *Festuca rubra* (red or fine fescue), *Lolium perenne* (perennial ryegrass), *Poa pratensis* (Kentucky bluegrass) and *Poa annua* (annual bluegrass).

According to a specific aspect of the invention, preferably R represents hydrogen or —$CO_2Et$.

Compounds of formula I above in which the groups $(R^2)_n$ are in the 2,4- or 2,3,4-positions of the benzoyl ring are also preferred.

Preferably $R^2$ is selected from the group consisting of halogen, —$S(O)_pR^4$ and —$CF_3$.

Preferably one of the groups $R^2$ represents —$S(O)_pR^4$, wherein $R^4$ is methyl.

Compounds of formula I above in which $(R^2)_n$ is 2-methylsulphonyl-4-trifluoromethyl or 2-methylsulphenyl-3,4-dichloro are especially preferred.

An especially preferred compound is ethyl 5-cyclopropyl-4-[3,4-dichloro-2-(methylsulphenyl)benzoyl]isoxazole-3-carboxylate.

The most preferred compound of the invention is 5-cyclopropyl-4-(2-methylsulphonyl-4-trifluoromethyl)benzoylisozaxole, hereafter referred to as Compound 1.

The effective amount of isoxazole derivative which is used in the invention is generally from 17 to 1000 g/ha, preferably from 50 to 800 g/ha. Where the locus comprises an unwanted turfgrass, such as one or more of *Cynodon dactylon* (bermudagrass), *Agrostis stolinifera* (creeping bentgrass), and *Dactylis glomerata* (orchardgrass), the isoxazole derivative is typically applied at a dose rate of from 50 to 800 g/ha, more preferably from 100 to 400 g/ha, even more preferably from 150 to 250 g/ha and most preferably about 202 g/ha.

The isoxazole derivative are preferably applied post-emergence of the or each turfgrass species, and it has been found that application to cool season turfgrasses is particularly effective. By the term "cool season turfgrasses" is meant turfgrasses which are found in temperate conditions It is also preferred to apply the isoxazole derivative of formula (I) above to established turfgrass areas, where the level of selectivity of the desired turfgrass is especially high.

Unless otherwise specified, the percentage cited in the instant specification are by weight.

The treatment of turf according to the invention is advantageously made by spraying a solid or liquid composition comprising the said isoxazole derivative.

The compositions which may be used in the invention for the treatment of the invention may comprise from 0.001 to 95% of the isoxazole derivative.

The liquid diluted formulations as applied to the turf comprise generally from 0.001 to 3% of isoxazole derivative, preferably from 0.1 to 0.5%.

The solid formulations as applied to the turf comprise generally from 0.1 to 8% of isoxazole derivative, preferably from 0.5 to 15%.

The concentrated compositions are the compositions which are commercialized or transported or stored. For application to plant they are normally diluted in water and applied in such a diluted form. The diluted form is part of the invention as well as the concentrated forms.

The concentrated formulations comprise generally from 5 to 95% of isoxazole derivative, preferably from 10 to 50%.

The concentrated compositions according to the invention may be in the form of a solid, e.g. dusts or granules or wettable powders, or, preferably, in the form of a liquid, such as an emulsifiable concentrate or a true solution.

The compositions according to the instant invention generally comprise from 0.5 to 95% of active ingredient, or preferably from 3 to 75% of active ingredient. The remaining part up to 100% comprises a carrier as well as various additives such as those here after indicated.

By "carrier", it is herein meant an organic or inorganic material, which may be natural of artificial or synthetic, and which is associated to the active ingredients and which facilitates its application to the turf. This carrier is thus generally inert and should be agriculturally acceptable, especially on the contemplated or treated turf. The carrier may be solid (clay, silicates, silica, resins, wax, fertilizers, etc.) or liquid (water, alcohols, ketones, oil solvent, saturated or unsaturated hydrocarbons, chlorinated hydrocarbons, liquefied gas, etc.).

Among the many additives, the compositions of the invention may comprise surfactants as well as dispersants or stickers or antifoam agent or antifreezing agents or dyestuffs or thickeners, or adhesives or protecting colloids, penetrating agents, stabilizing agents, sequestering agents, antiflocculating agents, corrosion inhibitors, pigments, polymers.

More generally the compositions of the invention may comprise all kind of solid or liquid additives which are known in the art.

The surfactant may be emulsifying or wetting, ionic or non ionic. Possible surfactants are salts of polyacrylic or lignosulfonic acids, salts of phenolsulfonic or naphthalenesulfonic acids; polycondensates of ethylene oxide with fatty alcohols or fatty acids or fatty amines or substituted phenols (particularly alkylphenols or arylphenols); esters-salts of sulfosuccinic acids, taurine derivatives, such as alkyl taurates; Phosphoric esters of alcohols or polyoxyethylated phenols. The use of at least one surfactant is generally required because the active ingredients are not water soluble while the spraying vehicle is water.

The method of application of the compositions of the invention is generally the spraying of a mixture which has been previously made by dilution of more concentrated formulations according to the invention.

Solid compositions may be powders for dusting or for dispersion and granule, especially extruded or compacted granules, or granules which have been made by impregnation of a powder (the content of active ingredients present in such powders will generally be from 1 to 80%).

Liquid compositions or compositions which have to be liquid when applied include solutions, water soluble concentrates emulsifiable concentrates, emulsions, wettable powders or pastes, water dispersible granules.

Emulsifiable concentrates comprise generally 10 to 80% of active ingredient; the emulsions when applied comprise generally 0.01 to 20% of active ingredient.

For example, the emulsifiable concentrates may comprise the solvent and further, as far as needed, 2 to 20% of suitable additives as stabilizers, surfactants, penetrating agents, corrosion inhibitors, or other additives already recited.

These concentrates are usually diluted in tank water so as to obtain the dilution appropriate for spraying.

The concentrated suspensions may also be applied by spraying and should be fluid without letting any solid to separate and falling at the bottom. Generally they comprise 1 to 75% of active ingredients (preferably 2 to 50%), 0.5 to 15% of surfactants, 0.1 to 10% of thickeners, 0 to 10% of other suitable additives as already indicated, and further water or an organic liquid wherein the active ingredient is insoluble or has a low solubility.

The wettable powders generally comprise the active ingredients (1 to 95%, preferably 2 to 80%), the solid carrier, a wetting agent (0 to 5%), a dispersing agent (3 to 10%) and, as far as needed, 0 to 10% of other additives such as stabilizers and other as already listed.

In order to obtain these wettable powders or dusting powders, it is appropriate to intimately mix the active ingredients and the additives, to grind in a mill or similar devices.

Dispersible granules are generally made by agglomeration of a powder followed by an appropriate granulation process.

The emulsions herein described may be of type oil-in water or water-in-oil. They may more or less thick, up to be like gels.

It will be understood that the composition or formulation used will vary depending to specific conditions of the treatment problem.

The compositions of the inventions may also be used in admixtures with another pesticide e.g. an insecticide, acaricide or herbicide, in particular with other herbicides approved for use in turfgrass areas.

The isoxazole derivatives used in the method of the invention are known from European Patent Publication Nos. 0418175, 0487537, 0527036 and 0560482, or can be prepared according to the methods described in these documents.

The invention is illustrated by the following examples which are not considered as limiting the invention but are given to better enable the skilled worker to use it. In the description that follows the following are trade marks: REAX, Sellogen, Barden, Aerosil, Igepal, Rhodafac, Biodac.

EXAMPLE 1

The following composition was prepared as a wettable dispersible granule (the percentages that follow are by weight):

| | |
|---|---|
| Isoxazole derivative (Compound 1): | 75.0% |
| REAX 88A (Surfactant): | 10.0% |
| Sellogen HR (Surfactant): | 3.0% |
| Barden AG-1 (Clay): | 11.0% |
| Aerosil R972 (Silica filler) | 1.0% |

This composition was then diluted in water and was sprayed on turfgrass plots as described below.

Turfgrass plugs, each of about 10.2 centimeter (cm) diameter, were taken in the field from established monoculture turfgrass stands consisting of a number of different turfgrass species. The plugs were established on sand culture pots for greenhouse study, the pots watered daily as needed to prevent drought stress and were mown to a height of 2 cm once a week. After 4 weeks the above composition was applied post-emergence at a number of dose rates to the species using a carbon dioxide backpack sprayer at a pressure of 152 kPa in 675 L/ha. Visual assessment was made of the injury to the turfgrasses over a period of 8 weeks after spraying. Also, the dry weights of the above-ground biomass of the pots was determined.

The results were as follows. Note that in Tables A1 to A3 the results are expressed as the percentage injury observed; in Tables A4 to A8 the percentage reduction in growth based on dry weight recoveries after 56 days (in comparison with the untreated control) is given.

TABLE A1

Results for turfgrass species *Poa pratensis* (Baron Kentucky bluegrass)

| Dose | Time after spraying (days) | | | | | | | |
|---|---|---|---|---|---|---|---|---|
| (g/ha) | 7 | 14 | 21 | 28 | 35 | 42 | 49 | 56 |
| 0 | 0.0 | 0.0 | 0.0 | 0.0 | 0.0 | 0.0 | 0.0 | 0.0 |
| 101 | 0.0 | 0.0 | 0.0 | 0.0 | 0.0 | 0.0 | 0.0 | 0.0 |
| 202 | 0.0 | 0.0 | 0.0 | 0.0 | 0.0 | 0.0 | 0.0 | 0.0 |
| 403 | 0.0 | 0.0 | 0.0 | 2.5 | 5.0 | 2.5 | 2.5 | 0.0 |
| 605 | 0.0 | 0.0 | 0.0 | 2.5 | 2.5 | 2.5 | 2.5 | 0.0 |
| 807 | 0.0 | 0.0 | 1.3 | 3.8 | 3.8 | 2.5 | 0.0 | 0.0 |

TABLE A2

Results for turfgrass species *Agrostis stolinifera* (GRN bentgrass, a creeping bentgrass)

| Dose | Time after spraying (days) | | | | | | | |
|---|---|---|---|---|---|---|---|---|
| (g/ha) | 7 | 14 | 21 | 28 | 35 | 42 | 49 | 56 |
| 0 | 12.5 | 20.0 | 20.0 | 22.5 | 23.8 | 22.5 | 22.5 | 22.5 |
| 101 | 13.8 | 42.5 | 58.8 | 60.0 | 57.5 | 57.0 | 54.5 | 59.5 |
| 202 | 32.5 | 77.5 | 85.0 | 87.0 | 83.3 | 87.0 | 88.3 | 87.0 |
| 403 | 41.3 | 86.3 | 95.0 | 98.3 | 99.5 | 99.5 | 99.5 | 99.8 |
| 605 | 46.3 | 87.5 | 97.5 | 98.8 | 99.5 | 99.5 | 99.5 | 99.5 |
| 807 | 47.5 | 88.8 | 96.3 | 99.5 | 100 | 100 | 100 | 100 |

TABLE A3

Results for turfgrass species *Agrostis stolinifera* (BK6 bentgrass, a creeping bentgrass)

| Dose | Time after spraying (days) | | | | | | | |
|---|---|---|---|---|---|---|---|---|
| (g/ha) | 7 | 14 | 21 | 28 | 35 | 42 | 49 | 56 |
| 0 | 0.0 | 0.0 | 0.0 | 0.0 | 0.0 | 0.0 | 0.0 | 0.0 |
| 101 | 18.8 | 47.5 | 56.3 | 56.3 | 37.0 | 32.5 | 31.3 | 25.0 |

TABLE A3-continued

Results for turfgrass species *Agrostis stolinifera* (BK6 bentgrass, a creeping bentgrass)

| Dose | Time after spraying (days) | | | | | | | |
|---|---|---|---|---|---|---|---|---|
| (g/ha) | 7 | 14 | 21 | 28 | 35 | 42 | 49 | 56 |
| 202 | 25.0 | 62.5 | 73.8 | 76.3 | 55.0 | 45.0 | 43.8 | 38.8 |
| 403 | 27.5 | 73.8 | 85.0 | 91.3 | 90.0 | 85.0 | 83.8 | 82.0 |
| 605 | 27.5 | 65.0 | 63.8 | 68.3 | 71.5 | 70.0 | 70.0 | 70.0 |
| 807 | 26.3 | 65.0 | 83.8 | 88.8 | 97.0 | 97.0 | 97.0 | 97.3 |

TABLE A4

Results for turfgrass species *Festuca arundinacea* (tall fescue)

| Dose Rate (g/ha) | Dry weight yield (in grams) | Percentage Yield Reduction |
|---|---|---|
| 0 | 1.1110 | N/A |
| 101 | 1.1550 | 0.0 |
| 202 | 1.0548 | 0.5 |
| 403 | 0.9795 | 11.8 |
| 605 | 0.7905 | 28.8 |
| 807 | 0.9580 | 13.8 |

TABLE A5

Results for turfgrass species *Lolium perenne* (perennial ryegrass)

| Dose Rate (g/ha) | Dry weight yield (in grams) | Percentage Yield Reduction |
|---|---|---|
| 0 | 1.3843 | N/A |
| 101 | 1.2128 | 12.4 |
| 202 | 1.1643 | 15.9 |
| 403 | 0.9803 | 29.2 |
| 605 | 1.0160 | 26.6 |
| 807 | 0.7873 | 43.1 |

TABLE A6

Results for turfgrass species *Festuca rubra* (red or fine fescue)

| Dose Rate (g/ha) | Dry weight yield (in grams) | Percentage Yield Reduction |
|---|---|---|
| 0 | 0.8738 | N/A |
| 101 | 0.9953 | 0 |
| 202 | 0.8330 | 4.7 |
| 403 | 0.7110 | 18.7 |
| 605 | 0.6113 | 30.0 |
| 807 | 0.4388 | 49.8 |

TABLE A7

Results for turfgrass species *Agrostis stolinifera* (Penncross creeping bentgrass)

| Dose Rate (g/ha) | Dry weight yield (in grams) | Percentage Yield Reduction |
|---|---|---|
| 0 | 2.2670 | N/A |
| 101 | 0.8290 | 63.4 |
| 202 | 0.6605 | 70.9 |
| 403 | 0.7050 | 68.9 |
| 605 | 0.5463 | 75.9 |
| 807 | 0.6570 | 71.0 |

TABLE A8

Results for turfgrass species *Agrostis stolinifera* (SDF bentgrass, a New England type creeping bentgrass)

| Dose Rate (g/ha) | Dry weight yield (in grams) | Percentage Yield Reduction |
|---|---|---|
| 0 | 2.0703 | N/A |
| 101 | 1.0753 | 48.1 |
| 202 | 0.8313 | 59.8 |
| 403 | 0.8118 | 60.8 |
| 605 | 0.7493 | 63.8 |
| 807 | 0.9418 | 54.5 |

These surprising results clearly show that it is possible to selectively control turfgrass species such as *Agrostis stolinifera* in the presence other turfgrass species such as *Poa pratensis, Lolium perenne, Festuca rubra* and *Festuca arundinacea*.

EXAMPLE 2

The following composition was prepared as a granule (the percentages that follow are by weight):

| | |
|---|---|
| Compound 1: | 0.38% |
| Igepal CA630 (surfactant): | 1.0% |
| Rhodafac RE610 (surfactant): | 1.0% |
| N-methylpyrollidine (solvent) | 7.0% |
| Biodac (20/40) (synthetic granule) | 90.62% |

The solid composition was spread pre-emergence of the weed species over a golf driving range which was an established unimproved turfgrass area, at the dose rates indicated below. The main turfgrass present was Lolium sp. (ryegrass). The turfgrass also comprised volunteer weed species including *Digitaria sanguinalis* (crabgrass) and *Trifolium repens* (White clover). Plots of about 4.65 square meters were treated pre-emergence of the above weed species with the composition at different dose rates (four replicates a each dose rate) and an untreated control. The percentage reduction in growth of the test species was determined by visual assessment 71 days after spraying in comparison with the untreated control. The results were as follows:

TABLE B1

| Dose Rate (g/ha) | DIGIS | TRFRE | LOLSS |
|---|---|---|---|
| 0 | 15.0 | 0.0 | 0.0 |
| 202 | 82.5 | 100 | 17.5 |
| 403 | 92.5 | 100 | 15.0 |

LOLSS = Lolium sp. (ryegrass)
DIGIS = *Digitaria sanguinalis* (crabgrass)
TRFRE = *Trifolium repens* (White clover)

What is claimed is:

1. A method for the selective control of an unwanted turfgrass or weed species in the presence of a desired turfgrass species at a turfgrass locus, said method comprising applying to said turfgrass locus a herbicidally effective amount of an isoxazole compound having the formula I:

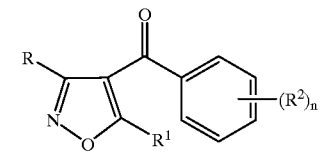

(I)

wherein:
R is hydrogen or —$CO_2R^3$;
$R^1$ is cyclopropyl;
$R^2$ is halogen, —$S(O)_pR^4$, $C_1$–$C_4$ alkyl or $C_1$–$C_4$ haloalkyl;
n is two or three;
p is zero, one or two;
$R^3$ is $C_1$–$C_4$ alkyl; and
$R^4$ is $C_1$–$C_4$ alkyl;
wherein said herbicidally effective amount of said compound of formula I is substantially more phytotoxic to said unwanted turfgrass or weed species than it is to said desired turfgrass species.

2. The method according to claim 1 wherein R represents hydrogen or —$CO_2Et$.

3. The method according to claim 2 wherein $R^2$ is selected from the group consisting of halogen, —$S(O)_pR^4$ and —$CF_3$.

4. The method according to claim 2 in which one of the groups $R^2$ represents —$S(O)_pR^4$ wherein $R^4$ is methyl.

5. The method according to claim 2 wherein the compound of formula I is applied under preventive conditions.

6. The method according to claim 2 wherein said locus comprises an established turfgrass stand.

7. The method according to claim 2 wherein the amount of isoxazole derivative which is applied is from 17 to 1000 g/ha.

8. The method according to claim 2 wherein the unwanted turfgrass is selected from the group consisting of *Cynodon dactylon, Agrostis stolinifera* and *Dactylis glomerata*.

9. The method according to claim 2 wherein the desired turfgrass is selected from the group consisting of *Festuca arundinacea, Festuca rubra, Lolium perenne, Poa piatensis* and *Poa annua*.

10. The method according to claim 9 wherein the unwanted turfgrass is selected from the group consisting of *Cynodon dactylon, Agrostis stolinifera* and *Dactylis glomerata*.

11. The method according to claim 1 wherein $R^2$ is selected from the group consisting of halogen, —$S(O)_pR^4$ and —$CF_3$.

12. The method according to claim 11 in which one of the groups $R^2$ represents —$S(O)_pR^4$, wherein $R^4$ is methyl.

13. The method according to claim 11 wherein the compound of formula I is applied under preventive conditions.

14. The method according to claim 11 wherein said locus comprises an established turfgrass stand.

15. The method according to claim 11 wherein the amount of isoxazole derivative which is applied is from 17 to 1000 g/ha.

16. The method according to claim 15 wherein the amount of isoxazole derivative which is used is from 50 to 800 g/ha.

17. The method according to claim 11 wherein the desired turfgrass is selected from the group consisting of *Festuca arundinacea, Festuca rubra, Lolium perenne, Poa piatensis* and *Poa annua*.

18. The method according to claim 17 wherein the unwanted turfgrass is selected from the group consisting of *Cynodon dactylon, Agrostis stolinifera* and *Dactylis glomerata*.

19. The method according to claim 11 wherein the unwanted turfgrass is selected from the group consisting of *Cynodon dactylon, Agrostis stolinifera* and *Dactylis glomerata*.

20. The method according to claim 1 in which one of the groups $R^2$ represents $-S(O)_pR^4$, wherein $R^4$ is methyl.

21. The method according to claim 20 wherein the compound of formula I is applied under preventive conditions.

22. The method according to claim 20 wherein said locus comprises an established turfgrass stand.

23. The method according to claim 20 wherein the amount of isoxazole derivative which is applied is from 17 to 1000 g/ha.

24. The method according to claim 23 wherein the amount of isoxazole derivative which is used is from 50 to 800 g/ha.

25. The method according to claim 20 wherein the desired turfgrass is selected from the group consisting of *Festuca arundinacea, Festuca rubra, Lolium perenne, Poa pratensis* and *Poa annua*.

26. The method according to claim 25 wherein the unwanted turfgrass is selected from the group consisting of *Cynodon dactylon, Agrostis stolinifera* and *Dactylis glomerata*.

27. The method according to claim 20 wherein the unwanted turfgrass is selected from the group consisting of *Cynodon dactylon, Agrostis stolinifera* and *Dactylis glomerata*.

28. The method according to claim 1 wherein the isoxazole derivative is 5-cyclopropyl4-(2-methylsulphonyl-4-trifluoromethyl)benzoylisozaxole.

29. The method according to claim 28 wherein the compound of formula I is applied under preventive conditions.

30. The method according to claim 28 wherein said locus comprises an established turfgrass stand.

31. The method according to claim 28 wherein the amount of isoxazole derivative which is applied is from 17 to 1000 g/ha.

32. The method according to claim 31 wherein the amount of isoxazole derivative which is used is from 50 to 800 g/ha.

33. The method according to claim 28 wherein the desired turfgrass is selected from the group consisting of *Festuca arundinacea, Festuca rubra, Lolium perenne, Poa pratensis* and *Poa annua*.

34. The method according to claim 33, wherein the unwanted turfgrass is selected from the group consisting of *Cynodon dactylon, Agrostis stolinifera* and *Dactylis glomerata*.

35. The method according to claim 28 wherein the unwanted turfgrass is selected from the group consisting of *Cynodon dactylon, Agrostis stolinifera* and *Dactylis glomerata*.

36. The method according to claim 1 wherein the compound of formula I is applied under preventive conditions.

37. The method according to claim 7 wherein the amount of isoxazole derivative which is used is from 50 to 800 g/ha.

38. The method according to claim 1 wherein said locus comprises an established turfgrass stand.

39. The method according to claim 1 wherein the amount of isoxazole derivative which is applied is from 17 to 1000 g/ha.

40. The method according to claim 39 wherein the amount of isoxazole derivative which is used is from 50 to 800 g/ha.

41. The method according to claim 1 wherein the desired turfgrass is selected from the group consisting of Festuca arundinacea, Festuca rubra, Lolium perenne, Poa pratensis and Poa annua.

42. The method according to claim 41 wherein the unwanted turfgrass is selected from the group consisting of *Cynodon dactylon, Agrostis stolinifera* and *Dactylis glomerata*.

43. The method according to claim 41 wherein the amount of isoxazole derivative applied is from 100 to 400 g/ha.

44. The method according to claim 43 wherein the amount of the isoxazole derivative applied is from 150 to 250 g/ha.

45. The method according to claim 1 wherein the unwanted turfgrass is selected from the group consisting of *Cynodon dactylon, Agrostis stolinifera* and *Dactylis glomerata*.

46. The method according to claim 45, wherein the amount of isoxazole derivative applied is from 100 to 400 g/ha.

47. The method according to claim 46 wherein the amount of the isoxazole derivative applied is from 150 to 250 g/ha.

48. The method according to claim 1 wherein the amount of isoxazole derivative applied is from 100 to 400 g/ha.

49. The method according to claim 48 wherein the amount of isoxazole derivative applied is from 150 to 250 g/ha.

* * * * *

UNITED STATES PATENT AND TRADEMARK OFFICE
CERTIFICATE OF CORRECTION

PATENT NO.    : 6,004,904
DATED         : December 21, 1999
INVENTOR(S)   : Thomas Edward Vrabel et al.

It is certified that error appears in the above-identified patent and that said Letters Patent is hereby corrected as shown below:

Title page,
Item "[56] References Cited", under "FOREIGN PATENT DOCUMENTS", second column, after "94/18179-8/1994 WIPO, add: -- 22736/88  4/1989 Australia --.

Signed and Sealed this

Twenty-eighth Day of August, 2001

*Attest:*

NICHOLAS P. GODICI
*Attesting Officer*   *Acting Director of the United States Patent and Trademark Office*